US005695935A

United States Patent [19]

Page et al.

[11] Patent Number: 5,695,935
[45] Date of Patent: Dec. 9, 1997

[54] DAZ: A GENE ASSOCIATED WITH AZOOSPERMIA

[75] Inventors: David C. Page, Winchester; Renee Reijo, Brookline, both of Mass.

[73] Assignee: Whitehead Institute for Biomedical Research, Cambridge, Mass.

[21] Appl. No.: 310,429

[22] Filed: Sep. 22, 1994

[51] Int. Cl.$^6$ .............................. C12Q 1/68; C12P 19/34; C07H 21/02; C07H 21/04
[52] U.S. Cl. .................. 435/6; 435/91.2; 536/23.1; 536/23.5; 536/24.3; 536/24.33
[58] Field of Search ............ 435/6, 91.2; 536/23.1, 536/23.5, 24.3, 24.33

[56] References Cited

PUBLICATIONS

Ma, K et al, Towards a molecular localization of the AZF locus; mapping of microdeletions in azoospermic men within 14 subintervals of interval 6 of the human Y chromosome, Hum. Mol. Genetic 1(1)29–33, 1992.

Ma, Kun et al., "A Y Chromosome Gene Family With RNA–Binding Protein Homology: Candidates for the Azoospermia Factor AZF Controlling Human Spermatogenesis", *Cell*, 75:1287–1295, (Dec. 31, 1993).

Foote, Simon et al., "The Human Y Chromosome: Overlapping DNA Clones Spanning the Euchromatic Region", *Science*, 258:60–66, (Oct. 2, 1992).

Vollrath, Douglas et al., "The Human Y Chromosome: A 43–Interval Map Based on Naturally Occurring Deletions", *Science*, 258:52–59, (Oct. 2, 1992).

*Primary Examiner*—W. Gary Jones
*Assistant Examiner*—Dianne Rees
*Attorney, Agent, or Firm*—Hamilton, Brook, Smith & Reynolds, P.C.

[57] ABSTRACT

Novel gene present in interval 6E and/or 6D of the distal portion of the long arm of the human Y chromosome, whose alteration is associated with reduced sperm count. Methods of diagnosis and treatment utilizing said gene, and antibodies that bind to the protein encoded by said gene.

14 Claims, 16 Drawing Sheets

FIG. 1

```
3/1
TCA GCT GGG GTC TAC TCC GAG GGT TCG CCC GAC CTT GGT TTT CCT TAC ACC TTA GCC TTT GGC TCC TTG ACC ACT CGA GCC CCA CAG GTG
 S   A   G   V   Y   S   E   G   S   P   D   L   G   F   P   Y   T   L   A   F   G   S   L   T   T   R   A   P   Q   V

93/31
TTC CAG CGG ACT TCA CCA GCA GAC CCA GAA GTG GGT GAA ACA CTG CCT CTG TTC CTC CTT GAG CCT GTC GGG AGC TGC CTG CAG CTA GCC
 F   Q   R   T   S   P   A   D   P   E   V   G   E   T   L   P   L   F   L   L   E   P   V   G   S   C   L   Q   L   A

183/61
CCA CCA TGT CTG CTG CAA ATC CTC AGA ACT CAA CCA TCT CCA GAG AGG CCA GCA CCC AGT CTT CAT CAG CTA CAG
 P   P   C   L   L   Q   I   L   R   T   Q   P   S   P   E   R   P   A   P   S   L   H   Q   L   Q

273/91
GCT GGG TGT TAC CAG AAG GCA AAA TCG TCA GTG AAA AGA ATT AGT AGG AAA ATG GAT GAA ACT GAG ATT GGA AGC
 A   G   C   Y   Q   K   A   K   S   S   V   K   R   I   S   R   K   M   D   E   T   E   I   G   S

363/121
TGC TTT GGT AGA TAC CAG AAG ATT AGT AGG AAA AGA ATT AGT AGG TCC AAA GGC TAT GGA TTT GTT TCG TTT GTT
 C   F   G   R   Y   Q   K   I   S   R   K   R   I   S   R   S   K   G   Y   G   F   V   S   F   V

453/151
AAT GAC GTG GAT GTC CAG AAG ATT AGT AGG AAT CAC GAA TCG AAC TGG TGT AAA AAG CTG AAG CTG GGC CCT GCA ATC AGG AAA CAA
 N   D   V   D   V   Q   K   I   S   R   N   H   E   S   N   W   C   K   K   L   K   L   G   P   A   I   R   K   Q

543/181
AAG TTA TGT GCT CGT CAT GTG GAT AAT CAC GAA TAC ATC TCC ATG GGT GTA GTT ACT CAG TAC GTT CAG TCT CCA AAT CCT GAG ACT CCA AAC TCA ACC
 K   L   C   A   R   H   V   D   N   H   E   Y   I   S   M   G   V   V   T   Q   Y   V   Q   S   P   N   P   E   T   P   N   S   T

633/211
ACT GAA ACC TAC CTG CAG CCC CAA ATC ACG CAA CCG AAT CCT GTA ACT CAG TAC GTT CAG TCT GCA AAT CCT GAG ACT CCA AAC TCA ACC
 T   E   T   Y   L   Q   P   Q   I   T   Q   P   N   P   V   T   Q   Y   V   Q   S   A   N   P   E   T   P   N   S   T

723/241
ATC TCC AGA GAG GCC AGC ACC CAG TCT TCA TCA GCT AGG ATG GAT GAA ACT GAG ATT GGA AGC CAA ACA CTG TTT
 I   S   R   E   A   S   T   Q   S   S   S   A   R   M   D   E   T   E   I   G   S   Q   T   L   F

813/271
GGT GGA ATC GAT GCT AGG ATG GAT GAA ACT GAG ATT GGA AGC CAA ACA CTG TTT
 G   G   I   D   A   R   M   D   E   T   E   I   G   S   Q   T   L   F

903/301
TTC GAA CTG GTG TGT CCA AGG CTA TGG ATT CGG CTC GTT GTT AAT GAC GTG GTT AGA AAG ATA GTA GGA GTA
 F   E   L   V   C   P   R   L   W   I   R   L   V   V   N   D   V   V   R   K   I   V   G   V
```

GAGTAATCAXATGCAXGTCATACTGAATTTGTACTGTATCACAGGTACTTCTTG

GAGAAGTGAAATGCTTGTGTTCAGACTATCAAAATTGTTAGCTTACAAATCAGG

TTTTAAAAACTTTTGGAAAGTCAGTATGTGCTTTTAAACACTTAAATGCAXGTC

TCAXTTTTTTTTTTTTTCCGXAGATATCTTAACATTCTTCAGTCTCGATTATGTG

TTACTTTAAACTATATATTAAACACAGACCCAGGTTCTAAATAAACATCTAATG

AAGAACAGCATCGTTAAGATAAAAACTAGAGAGTCTAATAATACAAGTTATAC

AGAAAGTTTCAGTGTGATTTCCAAATTCAGAATTTCAGTAATAGTGGAAAAACT

TTTAGCTTATATCACCCAGCACTCCCCATGAAACTAGATGCTGAGAGGCC

| FIG. 3A | FIG. 3B |
|---------|---------|
| FIG. 3C | FIG. 3D |

FIG. 3A

| YAC NO. | YAC Size (kb) | sY146Q | sY223 | sY209 | sY150 | sY207 | sY213 | sY142 | sY143 | sY216 | sY217 | sY153 | sY220 | sY240 | sY218 | sY150 | sY232 | sY233 | sY226 | sY249 | sY227 | sY205 | sY152 | sY149 | sY201 | sY203 | sY206 |
|---------|---------------|--------|-------|-------|-------|-------|-------|-------|-------|-------|-------|-------|-------|-------|-------|-------|-------|-------|-------|-------|-------|-------|-------|-------|-------|-------|-------|
| yOX5    | 460           |        |       |       |       |       | ▨     | ▨     |       |       |       |       |       |       |       |       |       |       |       |       |       |       |       |       |       |       |       |
| yOX40   | 600           |        |       |       |       |       |       |       |       | ▨     | ▨     |       |       |       |       |       |       |       |       |       |       |       |       |       |       |       |       |
| yOX21   | 640           |        |       |       |       |       |       |       |       |       |       | ▨     |       |       |       |       |       |       |       |       |       |       |       |       |       |       |       |
| yOX197  | 660           |        |       |       |       |       |       |       |       |       |       |       | ▨     | ▨     | ▨     | ▨     | ▨     | ▨     | ▨     | ▨     |       |       |       |       |       |       |       |
| yOX190  | 600           |        |       |       |       |       |       |       |       |       |       |       |       |       |       |       |       |       |       |       |       |       |       |       |       |       |       |
| yOX17   | 920           |        |       |       |       |       |       |       |       |       |       |       |       |       |       |       |       |       |       |       |       |       |       |       | ▨     | ▨     | ▨     |
| yOX50   | 550           |        |       |       |       |       |       |       |       |       |       |       |       |       |       |       |       |       |       |       |       |       |       |       |       |       |       |

| PATIENT NO. | Category |
|---|---|
| 2475 | Terminal Deletion |
| 1305 | Terminal Deletion |
| 1310 | Terminal Deletion |
| 1318 | Terminal Deletion |
| 2064 | Terminal Deletion |
| 746 | Terminal Deletion |
| 1788 | Terminal Deletion |
| 2240 | Terminal Deletion |
| 2168 | Terminal Deletion |
| 496 | Terminal Deletion |
| 2229 | Terminal Deletion |
| 1078 | Terminal Deletion |
| 1659 | Normal, Fertile |
| 2376 | Infertile |
| 2381 | Infertile |
| 2415 | Infertile |
| 2430 | Infertile |
| 2613 | Infertile |
| 2615 | Infertile |
| 2564 | Infertile |
| KLARD | Infertile |
| KUPAU | Infertile |
| MKB | Infertile |

FIG. 3C

| FIG. 4C | FIG. 4F | FIG. 4I |
|---------|---------|---------|
| FIG. 4B | FIG. 4E | FIG. 4H |
| FIG. 4A | FIG. 4D | FIG. 4G |

Figure 4J

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 975 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 1..975

( x i ) SEQUENCE DESCRIPTION: SEQ ID NO:1:

| TCA | GCT | GGG | GTC | TAC | TCC | GAG | GGT | TCG | CCC | GAC | CTT | GGT | TTT | CCT | TAC | 48 |
|---|---|---|---|---|---|---|---|---|---|---|---|---|---|---|---|---|
| Ser | Ala | Gly | Val | Tyr | Ser | Glu | Gly | Ser | Pro | Asp | Leu | Gly | Phe | Pro | Tyr | |
| 1 | | | | 5 | | | | | 10 | | | | | 15 | | |

| ACC | TTA | GCC | TTT | GGC | TCC | TTG | ACC | ACT | CGA | GCC | CCA | CAG | GTG | TTC | CAG | 96 |
|---|---|---|---|---|---|---|---|---|---|---|---|---|---|---|---|---|
| Thr | Leu | Ala | Phe | Gly | Ser | Leu | Thr | Thr | Arg | Ala | Pro | Gln | Val | Phe | Gln | |
| | | | 20 | | | | | 25 | | | | | 30 | | | |

| CGG | ACT | TCA | CCA | GCA | GAC | CCA | GAA | GTG | GTG | GGT | GAA | ACA | CTG | CCT | CTG | 144 |
|---|---|---|---|---|---|---|---|---|---|---|---|---|---|---|---|---|
| Arg | Thr | Ser | Pro | Ala | Asp | Pro | Glu | Val | Val | Gly | Glu | Thr | Leu | Pro | Leu | |
| | | 35 | | | | | 40 | | | | | 45 | | | | |

| TTC | CTC | CTT | GAG | CCT | GTC | GGG | AGC | TGC | TGC | CTG | CCA | CCA | CCA | TGT | CTG | 192 |
|---|---|---|---|---|---|---|---|---|---|---|---|---|---|---|---|---|
| Phe | Leu | Leu | Glu | Pro | Val | Gly | Ser | Cys | Cys | Leu | Pro | Pro | Pro | Cys | Leu | |
| | 50 | | | | | 55 | | | | | 60 | | | | | |

| CTG | CAA | ATC | CTG | AGA | CTC | CAA | ACT | CAA | CCA | TCT | CCA | GAG | AGG | CCA | GCA | 240 |
|---|---|---|---|---|---|---|---|---|---|---|---|---|---|---|---|---|
| Leu | Gln | Ile | Leu | Arg | Leu | Gln | Thr | Gln | Pro | Ser | Pro | Glu | Arg | Pro | Ala | |
| 65 | | | | | 70 | | | | | 75 | | | | | 80 | |

| CCC | AGT | CTT | CAT | CAG | CTG | CAG | CTA | GCC | AAG | GCT | GGG | TGT | TAC | CAG | AAG | 288 |
|---|---|---|---|---|---|---|---|---|---|---|---|---|---|---|---|---|
| Pro | Ser | Leu | His | Gln | Leu | Gln | Leu | Ala | Lys | Ala | Gly | Cys | Tyr | Gln | Lys | |
| | | | | 85 | | | | | 90 | | | | | 95 | | |

| GCA | AAA | TCG | TGC | CAA | ACA | CTG | TTT | TTT | GTT | GGT | GGA | ATT | GAT | GCT | AGG | 336 |
|---|---|---|---|---|---|---|---|---|---|---|---|---|---|---|---|---|
| Ala | Lys | Ser | Cys | Gln | Thr | Leu | Phe | Phe | Val | Gly | Gly | Ile | Asp | Ala | Arg | |
| | | | 100 | | | | | 105 | | | | | 110 | | | |

| ATG | GAT | GAA | ACT | GAG | ATT | GGA | AGC | TGC | TTT | GGT | AGA | TAC | GGT | TCA | GTG | 384 |
|---|---|---|---|---|---|---|---|---|---|---|---|---|---|---|---|---|
| Met | Asp | Glu | Thr | Glu | Ile | Gly | Ser | Cys | Phe | Gly | Arg | Tyr | Gly | Ser | Val | |
| | | | 115 | | | | | 120 | | | | | 125 | | | |

| AAA | AGA | AGT | GAA | GAT | AAT | CAC | GAA | TCG | AAC | TGG | TGT | TCC | AAA | GGC | TAT | 432 |
|---|---|---|---|---|---|---|---|---|---|---|---|---|---|---|---|---|
| Lys | Arg | Ser | Glu | Asp | Asn | His | Glu | Ser | Asn | Trp | Cys | Ser | Lys | Gly | Tyr | |
| | | 130 | | | | | 135 | | | | | 140 | | | | |

| GGA | TTT | GTT | TCG | TTT | GTT | AAT | GAC | GTG | GAT | GTC | CAG | AAG | ATT | AGT | AGG | 480 |
|---|---|---|---|---|---|---|---|---|---|---|---|---|---|---|---|---|
| Gly | Phe | Val | Ser | Phe | Val | Asn | Asp | Val | Asp | Val | Gln | Lys | Ile | Ser | Arg | |
| 145 | | | | | 150 | | | | | 155 | | | | | 160 | |

| ATC | ACA | GAA | TAC | ATC | TCC | ATG | GGT | AAA | AAG | CTG | AAG | CTG | GGC | CCT | GCA | 528 |
|---|---|---|---|---|---|---|---|---|---|---|---|---|---|---|---|---|
| Ile | Thr | Glu | Tyr | Ile | Ser | Met | Gly | Lys | Lys | Leu | Lys | Leu | Gly | Pro | Ala | |
| | | | | 165 | | | | | 170 | | | | | 175 | | |

| ATC | AGG | AAA | CAA | AAG | TTA | TGT | GCT | CGT | CAT | GTG | CAG | CCA | CGT | CCT | TTG | 576 |
|---|---|---|---|---|---|---|---|---|---|---|---|---|---|---|---|---|
| Ile | Arg | Lys | Gln | Lys | Leu | Cys | Ala | Arg | His | Val | Gln | Pro | Arg | Pro | Leu | |
| | | | 180 | | | | | 185 | | | | | 190 | | | |

| GTA | GTT | AAT | CCT | CCT | CCT | CCA | CCA | CAG | TTT | CAG | AAC | GTC | TGG | CGG | AAT | 624 |
|---|---|---|---|---|---|---|---|---|---|---|---|---|---|---|---|---|
| Val | Val | Asn | Pro | Pro | Pro | Pro | Pro | Gln | Phe | Gln | Asn | Val | Trp | Arg | Asn | |
| | | 195 | | | | | 200 | | | | | 205 | | | | |

| CCA | AAC | ACT | GAA | ACC | TAC | CTG | CAG | CCC | CAA | ATC | ACG | CCG | AAT | CCT | GTA | 672 |
|---|---|---|---|---|---|---|---|---|---|---|---|---|---|---|---|---|
| Pro | Asn | Thr | Glu | Thr | Tyr | Leu | Gln | Pro | Gln | Ile | Thr | Pro | Asn | Pro | Val | |
| | 210 | | | | | 215 | | | | | 220 | | | | | |

| ACT | CAG | TAC | GTT | CAG | TCT | GCT | GCA | AAT | CCT | GAG | ACT | CCA | AAC | TCA | ACC | 720 |
|---|---|---|---|---|---|---|---|---|---|---|---|---|---|---|---|---|
| Thr | Gln | Tyr | Val | Gln | Ser | Ala | Ala | Asn | Pro | Glu | Thr | Pro | Asn | Ser | Thr | |

```
                     225                           230                           235                           240
ATC   TCC   AGA   GAG   GCC   AGC   ACC   CAG   TCT   TCA   TCA   GCT   GCA   GCT   AGC   CAA                   768
Ile   Ser   Arg   Glu   Ala   Ser   Thr   Gln   Ser   Ser   Ser   Ala   Ala   Ala   Ser   Gln
                        245                           250                           255

GGC   TGG   GTG   TTA   CCA   GAA   GGC   AAA   ATC   GGC   CAA   ACA   CTG   TTT   GGT   GGT                   816
Gly   Trp   Val   Leu   Pro   Glu   Gly   Lys   Ile   Gly   Gln   Thr   Leu   Phe   Gly   Gly
                        260                           265                           270

GGA   ATC   GAT   GCT   AGG   ATG   GAT   GAA   ACT   GAG   ATT   GGA   AGC   TGC   TTT   GGT                   864
Gly   Ile   Asp   Ala   Arg   Met   Asp   Glu   Thr   Glu   Ile   Gly   Ser   Cys   Phe   Gly
                        275                           280                           285

AGA   TAC   GGC   TCA   GAG   AAA   GAA   GTG   AAG   ATA   TCA   CGA   TTC   GAA   CTG   GTG                   912
Arg   Tyr   Gly   Ser   Glu   Lys   Glu   Val   Lys   Ile   Ser   Arg   Phe   Glu   Leu   Val
            290                           295                           300

TGT   CCA   AGG   CTA   TGG   ATT   CGG   CTC   GTT   GTT   AAT   GAC   GTC   GTG   TTC   AGA                   960
Cys   Pro   Arg   Leu   Trp   Ile   Arg   Leu   Val   Val   Asn   Asp   Val   Val   Phe   Arg
305                           310                           315                           320

AAG   ATA   GTA   GGA   GTA                                                                                     975
Lys   Ile   Val   Gly   Val
                        325
```

( 2 ) INFORMATION FOR SEQ ID NO:2:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser   Ala   Gly   Val   Tyr   Ser   Glu   Gly   Ser   Pro   Asp   Leu   Gly   Phe   Pro   Tyr
1                       5                             10                            15

Thr   Leu   Ala   Phe   Gly   Ser   Leu   Thr   Thr   Arg   Ala   Pro   Gln   Val   Phe   Gln
                        20                            25                            30

Arg   Thr   Ser   Pro   Ala   Asp   Pro   Glu   Val   Val   Gly   Glu   Thr   Leu   Pro   Leu
                  35                          40                            45

Phe   Leu   Leu   Glu   Pro   Val   Gly   Ser   Cys   Cys   Leu   Pro   Pro   Pro   Cys   Leu
            50                          55                            60

Leu   Gln   Ile   Leu   Arg   Leu   Gln   Thr   Gln   Pro   Ser   Pro   Glu   Arg   Pro   Ala
65                            70                            75                            80

Pro   Ser   Leu   His   Gln   Leu   Gln   Leu   Ala   Lys   Ala   Gly   Cys   Tyr   Gln   Lys
                        85                            90                            95

Ala   Lys   Ser   Cys   Gln   Thr   Leu   Phe   Phe   Val   Gly   Gly   Ile   Asp   Ala   Arg
                  100                         105                           110

Met   Asp   Glu   Thr   Glu   Ile   Gly   Ser   Cys   Phe   Gly   Arg   Tyr   Gly   Ser   Val
            115                         120                           125

Lys   Arg   Ser   Glu   Asp   Asn   His   Glu   Ser   Asn   Trp   Cys   Ser   Lys   Gly   Tyr
      130                         135                           140

Gly   Phe   Val   Ser   Phe   Val   Asn   Asp   Val   Asp   Val   Gln   Lys   Ile   Ser   Arg
145                         150                           155                           160

Ile   Thr   Glu   Tyr   Ile   Ser   Met   Gly   Lys   Lys   Leu   Lys   Leu   Gly   Pro   Ala
                        165                           170                           175

Ile   Arg   Lys   Gln   Lys   Leu   Cys   Ala   Arg   His   Val   Gln   Pro   Arg   Pro   Leu
                  180                         185                           190

Val   Val   Asn   Pro   Pro   Pro   Pro   Gln   Phe   Gln   Asn   Val   Trp   Arg   Asn
            195                         200                           205

Pro   Asn   Thr   Glu   Thr   Tyr   Leu   Gln   Pro   Gln   Ile   Thr   Pro   Asn   Pro   Val
                  210                         215                           220
```

| Thr 225 | Gln | Tyr | Val | Gln | Ser 230 | Ala | Ala | Asn | Pro | Glu 235 | Thr | Pro | Asn | Ser | Thr 240 |
|---|---|---|---|---|---|---|---|---|---|---|---|---|---|---|---|
| Ile | Ser | Arg | Glu | Ala 245 | Ser | Thr | Gln | Ser | Ser 250 | Ser | Ala | Ala | Ala | Ser 255 | Gln |
| Gly | Trp | Val | Leu 260 | Pro | Glu | Gly | Lys | Ile 265 | Gly | Gln | Thr | Leu 270 | Phe | Gly | Gly |
| Gly | Ile | Asp 275 | Ala | Arg | Met | Asp | Glu 280 | Thr | Glu | Ile | Gly | Ser 285 | Cys | Phe | Gly |
| Arg | Tyr 290 | Gly | Ser | Glu | Lys | Glu 295 | Val | Lys | Ile | Ser | Arg 300 | Phe | Glu | Leu | Val |
| Cys 305 | Pro | Arg | Leu | Trp | Ile 310 | Arg | Leu | Val | Val | Asn 315 | Asp | Val | Val | Phe | Arg 320 |
| Lys | Ile | Val | Gly | Val 325 | | | | | | | | | | | |

( 2 ) INFORMATION FOR SEQ ID NO:3:

( i ) SEQUENCE CHARACTERISTICS:
( A ) LENGTH: 428 base pairs
( B ) TYPE: nucleic acid
( C ) STRANDEDNESS: double
( D ) TOPOLOGY: linear ( x i ) SEQUENCE DESCRIPTION: SEQ ID NO:3:

| GAGTAATCAN | ATGCANGTCA | TACTGAATTT | GTACTGTATC | ACAGGTACTT | CTTGGAGAAG | 60 |
|---|---|---|---|---|---|---|
| TGAAATGCTT | GTGTTCAGAC | TATCAAAATT | GTTAGCTTAC | AAATCAGGTT | TTAAAAACTT | 120 |
| TTGGAAAGTC | AGTATGTGCT | TTTAAACACT | TAAATGCANG | TCTCANTTTT | TTTTTTTTC | 180 |
| CGNAGATATC | TTAACATTCT | TCAGTCTCGA | TTATGTGTTA | CTTTAAACTA | TATATTAAAC | 240 |
| ACAGACCCAG | GTTCTAAATA | AACATCTAAT | GAAGAACAGC | ATCGTTAAGA | TAAAAACTAG | 300 |
| AGAGTCTAAT | AATACAAGTT | ATACAGAAAG | TTTCAGTGTG | ATTTCCAAAT | TCAGAATTTC | 360 |
| AGTAATAGTG | GAAAAACTTT | TAGCTTATAT | CACCCAGCAC | TCCCCATGAA | ACTAGATGCT | 420 |
| GAGAGGCC | | | | | | 428 |

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( x i ) SEQUENCE DESCRIPTION: SEQ ID NO:4:

GGGTGTTACC AGAAGGCAAA                                      20

( 2 ) INFORMATION FOR SEQ ID NO:5:

( i ) SEQUENCE CHARACTERISTICS:
( A ) LENGTH: 22 base pairs
( B ) TYPE: nucleic acid
( C ) STRANDEDNESS: double
( D ) TOPOLOGY: linear ( x i ) SEQUENCE DESCRIPTION: SEQ ID NO:5:

GAACCGTATC TACCAAAGCA GC                                   22

( 2 ) INFORMATION FOR SEQ ID NO:6:

( i ) SEQUENCE CHARACTERISTICS:
( A ) LENGTH: 20 base pairs
( B ) TYPE: nucleic acid (C) STRANDEDNESS: double
        (D) TOPOLOGY: linear (xi) SEQUENCE DESCRIPTION: SEQ ID NO:6:

GTTACAGGAT TCGGCGTGAT                                                                                    20

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (xi) SEQUENCE DESCRIPTION: SEQ ID NO:7:

CTCGTCATGT GCAGCCAC                                                                                      18

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:8:

GCTGCAAATC CTGAGACTCC                                                                                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:9:

TTTGCCTTCT GGTAACACCC                                                                                    20

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Leu  Phe  Val  Gly  Asn  Leu
    1                   5

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Ile  Tyr  Ile  Lys  Gly  Met
    1                   5

(2) INFORMATION FOR SEQ ID NO:12:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:12:

Leu Phe Val Gly Gly Ile
1               5

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Lys Gly Tyr Gly Phe Val Xaa Phe
1               5

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Lys Gly Tyr Gly Phe Val Asn Phe
1               5

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Lys Gly Tyr Gly Phe Val Ser Phe
1               5

DAZ: A GENE ASSOCIATED WITH AZOOSPERMIA

FUNDING

Work described herein was supported by grant RO1-HGO0257 from the National Institute of Health, National Center for Genome Research, funding from the Howard Hughes Foundation and funding from the Damon Runyon-Walter Winchell Foundation Cancer Research Fund. The United States Government has certain rights in the invention.

BACKGROUND OF THE INVENTION

Male infertility is a concern for many couples. Worldwide studies have shown that 2%–7% of all couples have experienced difficulty in achieving conception or a complete inability to bear children, especially as they near the end of their reproductive life. (Sara A., *Advances in Fertility and Sterility, Proc. Twelfth World Congress Fer. Steril.* 4: 91–92 (1987)). Furthermore, among men who seek help or advice at fertility clinics, slightly more than 10% are diagnosed as being oligospermic or azoospermic for unknown reasons. (Hatgreave, T. B., *The Management of Male Infertility*, T. B. Hargreave and T. E. Soon, eds. (Singapore: PG Publishing, pp. 2–21, 1990)). At this time, little is known about the causes of reduced spermatogenesis and, although various treatments are available, none is a completely satisfactory alternative.

SUMMARY OF THE INVENTION

This invention pertains to a gene present in interval 6E of the distal portion of the long arm of the human Y chromosome, whose alteration is associated with reduced sperm count. This gene, which appears to be testis-specific, is approximately 3.1 kb in size, and encodes a protein homologous in certain domains to several RNA binding proteins.

The present invention also relates to a method of diagnosing reduced sperm count associated with alteration of a gene in interval 6E of the distal portion of the long arm of the Y chromosome and particularly to a method of diagnosing reduced sperm count associated with alteration of the gene described herein and referred to as the DAZ gene. In one embodiment of the present method, deletion of the gene is assessed, such as by a hybridization method in which a nucleic acid sequence which hybridizes to the gene described herein (or portion of that gene) is used to assess Y chromosome DNA for the presence or absence of the gene. For example, lack of hybridization of the nucleic acid used to a DNA sample obtained from a male who has a reduced sperm count indicates that the gene is deleted and that the reduced sperm count is associated with the deletion. The present invention also relates to nucleotide sequences for use as probes or primers for methods of diagnosing reduced sperm count associated with alteration of the gene described herein.

The present invention further relates to the encoded protein, which includes the amino acid sequence of the RNA binding domains conserved among members of the family of RNA binding proteins. This invention also relates to a method of treating reduced sperm count, such as by a gene therapy method in which the gene described herein, or a gene portion which encodes a functional protein, is introduced into a man whose sperm count is reduced and in whom the gene is expressed and the encoded protein replaces the protein normally produced or enhances the quantity produced.

The novel gene described herein has been designated the DAZ gene, and has been shown to be altered in men whose sperm count is reduced. It is located exclusively within the 6E deletion interval, appears to encode a testis-specific transcript, is present in a single copy on the Y chromosome of higher primates, and probably has a homologue in lower mammals.

Thus, this invention has application to several areas. It may be used diagnostically to identify males with reduced sperm count in whom the gene has been altered. It may also be used therapeutically in gene therapy treatments to remedy fertility disorders associated with alteration of the gene. This invention also has application as a research tool, as the nucleic acid sequence has been localized to interval 6E of the distal portion of the long arm of the human Y chromosome and can therefore serve as a marker for the interval.

BRIEF DESCRIPTION OF THE DRAWINGS

FIG. 1 is a partial nucleotide sequence of the DAZ gene (SEQ ID NO.: 1) with the corresponding amino acid sequence (SEQ ID NO.: 2) indicated underneath.

FIG. 2 is a partial sequence of the DAZ gene (SEQ ID NO.: 3); the partial sequence represented by SEQ ID NO.: 3 is 5' of the partial sequence represented by SEQ ID NO.: 1.

FIGS. 3A, 3B, 3C, 3D are a map of patient deletions and YAC clones spanning the entire interval. The numbers proceeded by "yS" along the top margin are sequence-tagged sites (STS). The letters "na" indicate that the site was not analyzed. FIG. 3 is a schematic of the relationship between FIGS. 3A, 3B, 3C and 3D.

FIGS. 4A through 4I represent the deletion map; FIG. 4J is an overview of FIGS. 4A through 4I.

FIGS. 4A through 4J taken from Vollrath et al., *Science* 258: 52–59 (1992).

DETAILED DESCRIPTION OF THE INVENTION

The present invention pertains to a novel gene present in interval 6E of the distal portion of the long arm of the human Y chromosome, whose alteration is associated with reduced sperm count. As described herein, Applicants have studied the Y chromosome of infertile males, their fathers and normal males. Among 71 infertile males, 8 males have been identified who have de novo overlapping interstitial deletions on the distal long arm of the Y-chromosome; no such deletions were detected in normal males. The size of the deletion interval which contains this gene is approximately 500 kb.

Figure 3B:
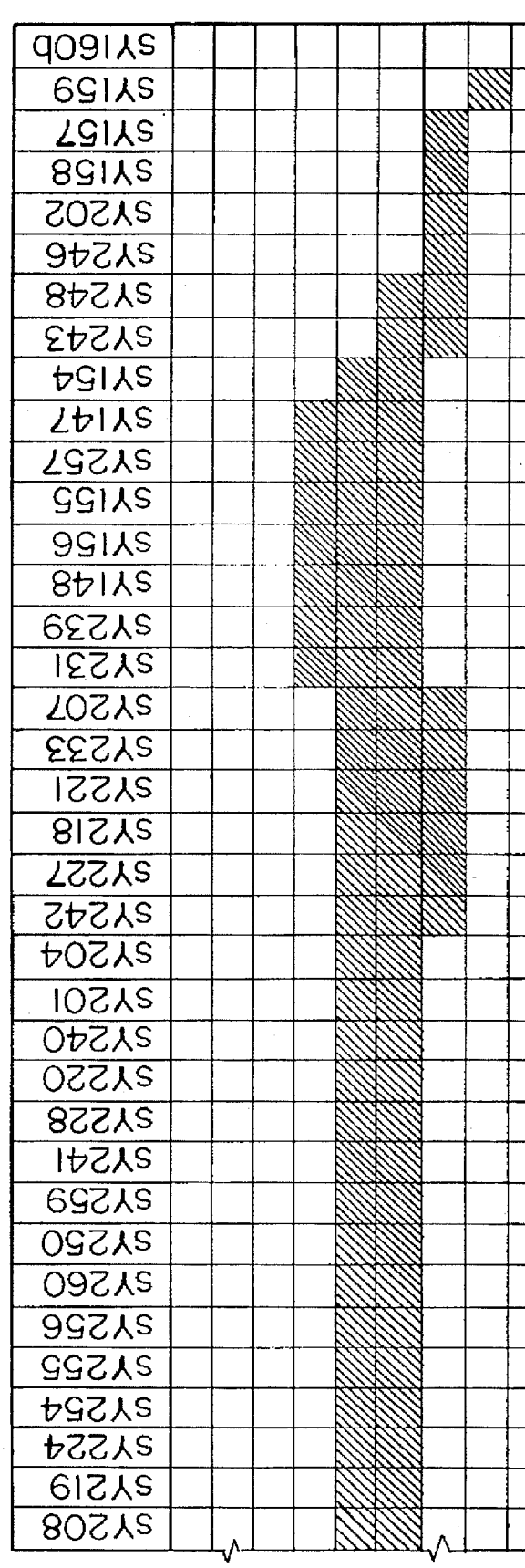
Figure 3D:
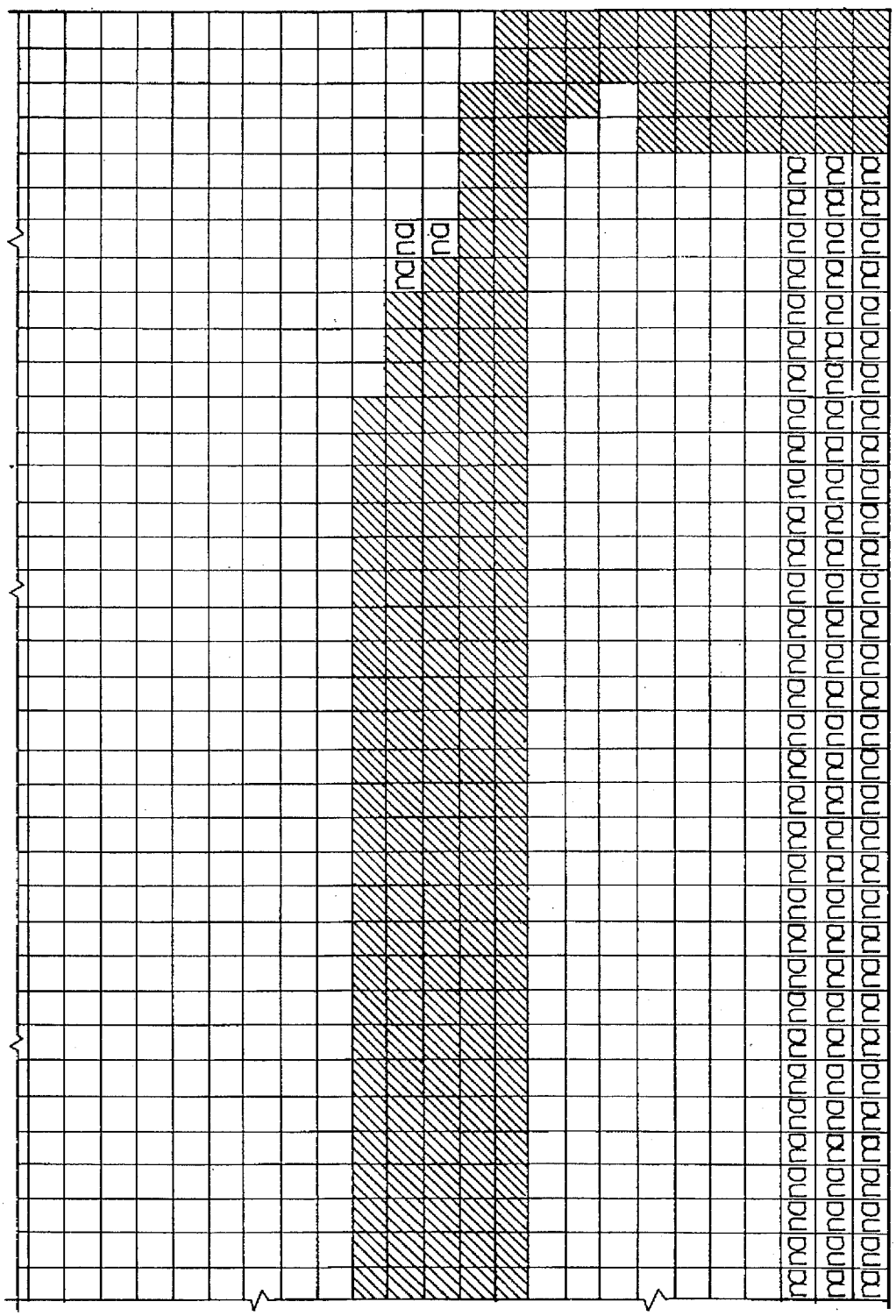
Figure 4A:
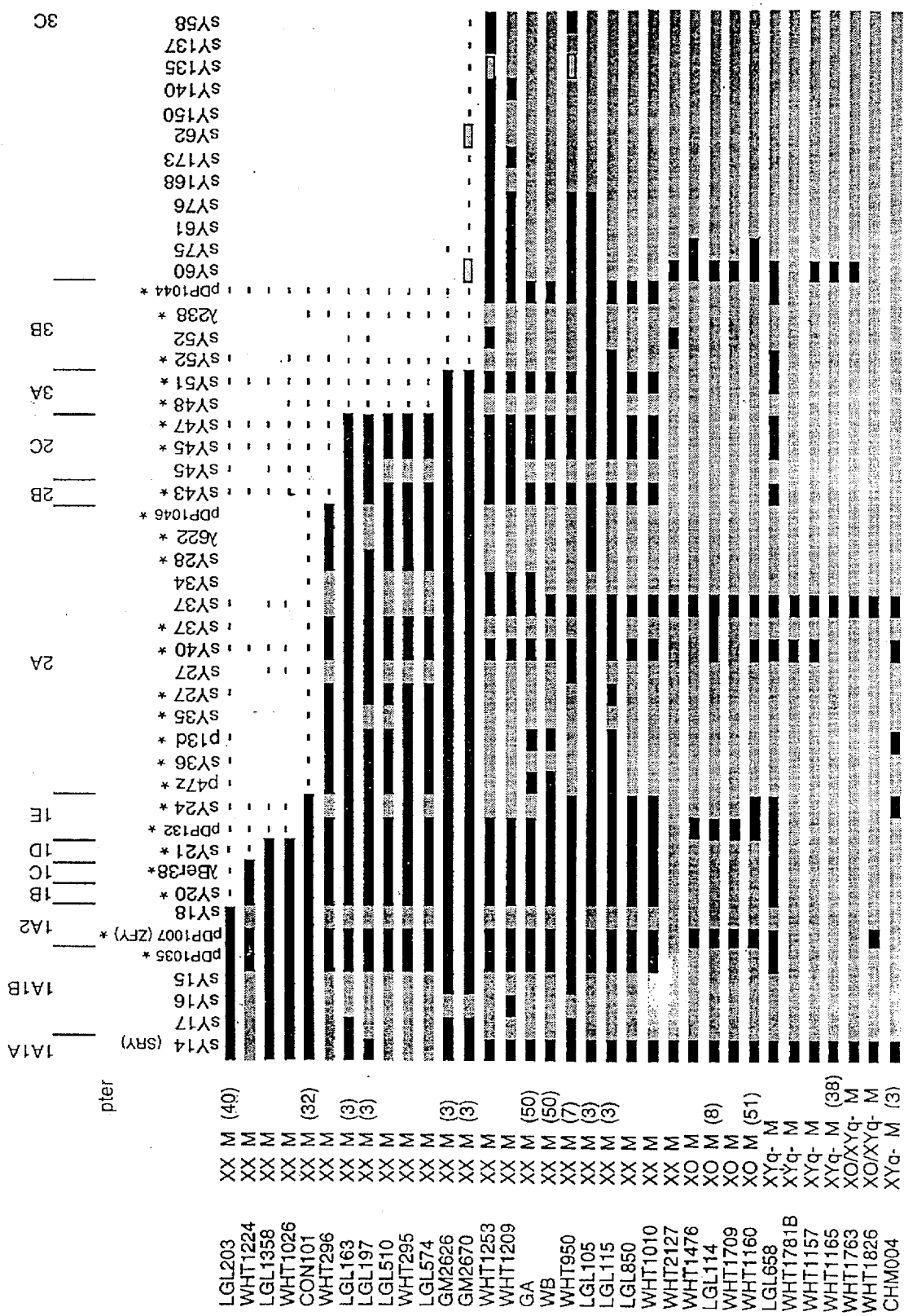
FIGS. 4A and 4B are a 43-interval deletion map of the human Y chromosome. Along the left border are listed 96 individuals who carry part but not all of the Y chromosome (abbreviated karyotypes are given; M, male; F, female; H, hemaphrodite). Along the top margin are listed deletion intervals 1A1A through 7. Listed immediately below the intervals are 132 Y-chromosomal DNA loci comprising 122 STS's and ten unsequenced plasmid or phage clones. The experimentally demonstrated presence of a locus in an individual is indicated by a black segment; the inferred presence (by extrapolation) of a locus in an individual is indicated by a gray segment. Experimentally demonstrated absence is indicated by a minus, and inferred absence is indicated by the absence of any symbol. White boxes represent positive PCR results, and gray boxes represent a few PCR results for repeated or X-Y homologous loci that are positive but of reduced strength relative to results obtained with normal males.
Figure 4B:
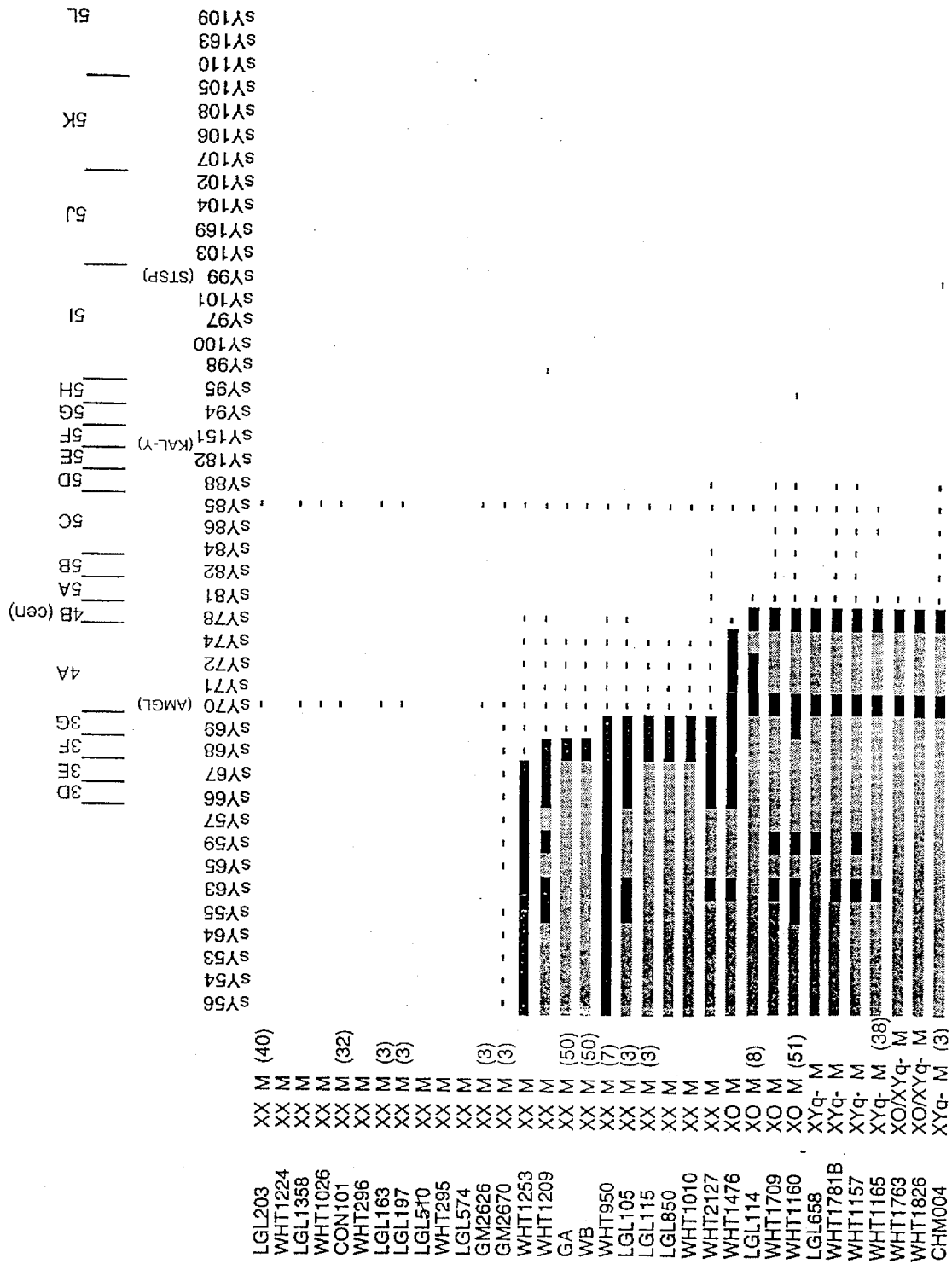
Figure 4C:
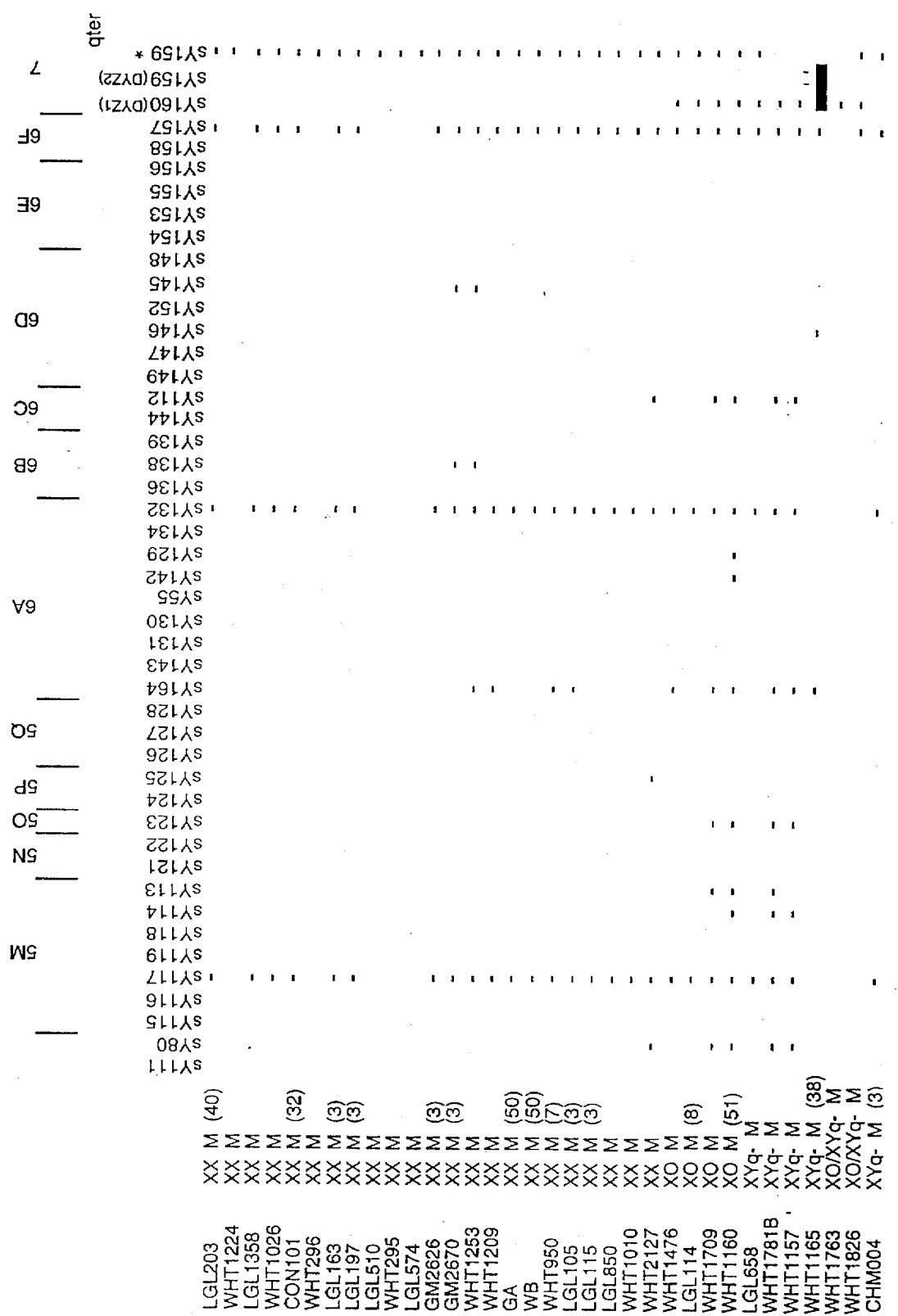
Figure 4D:
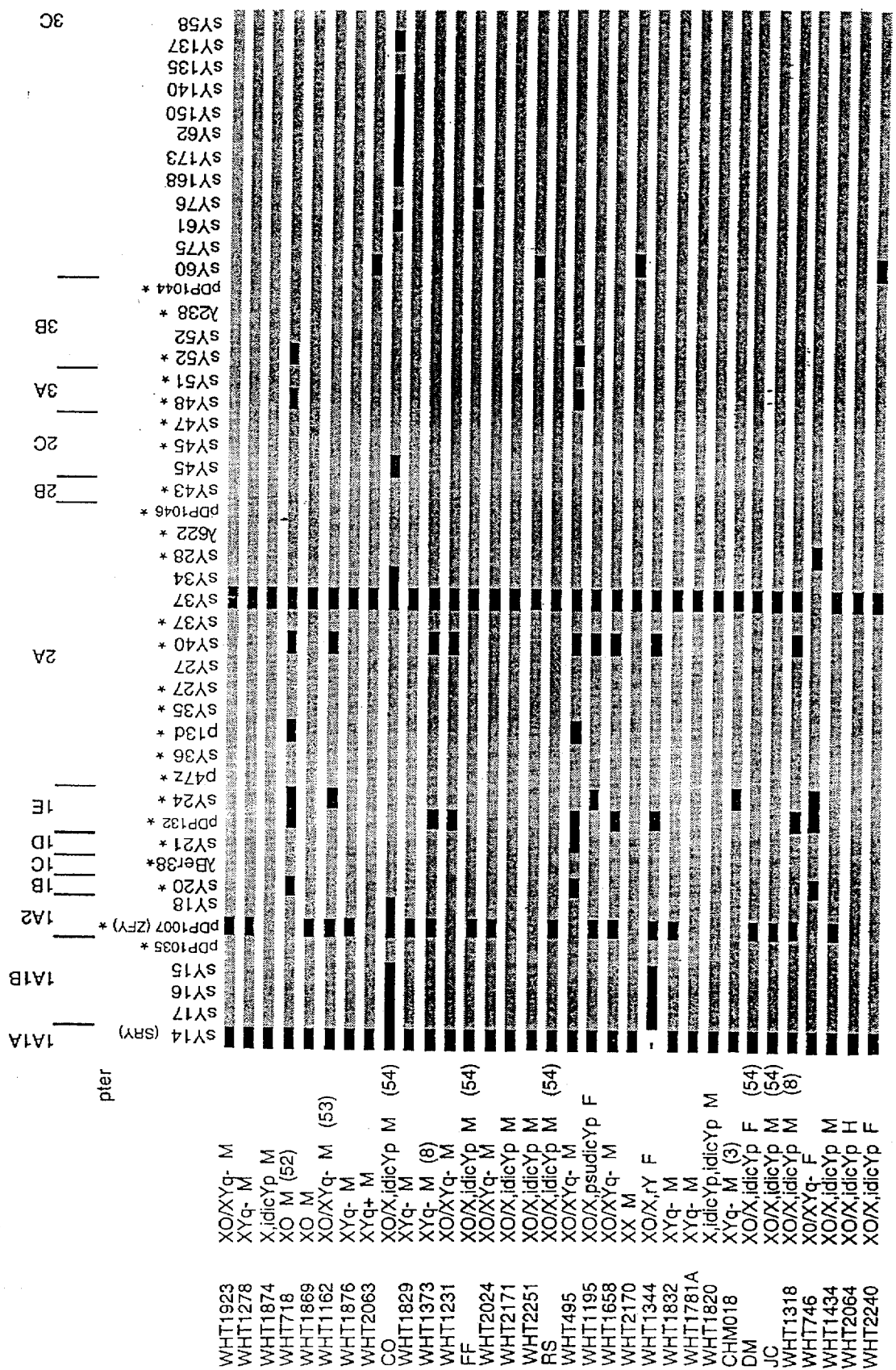
Figure 4E:
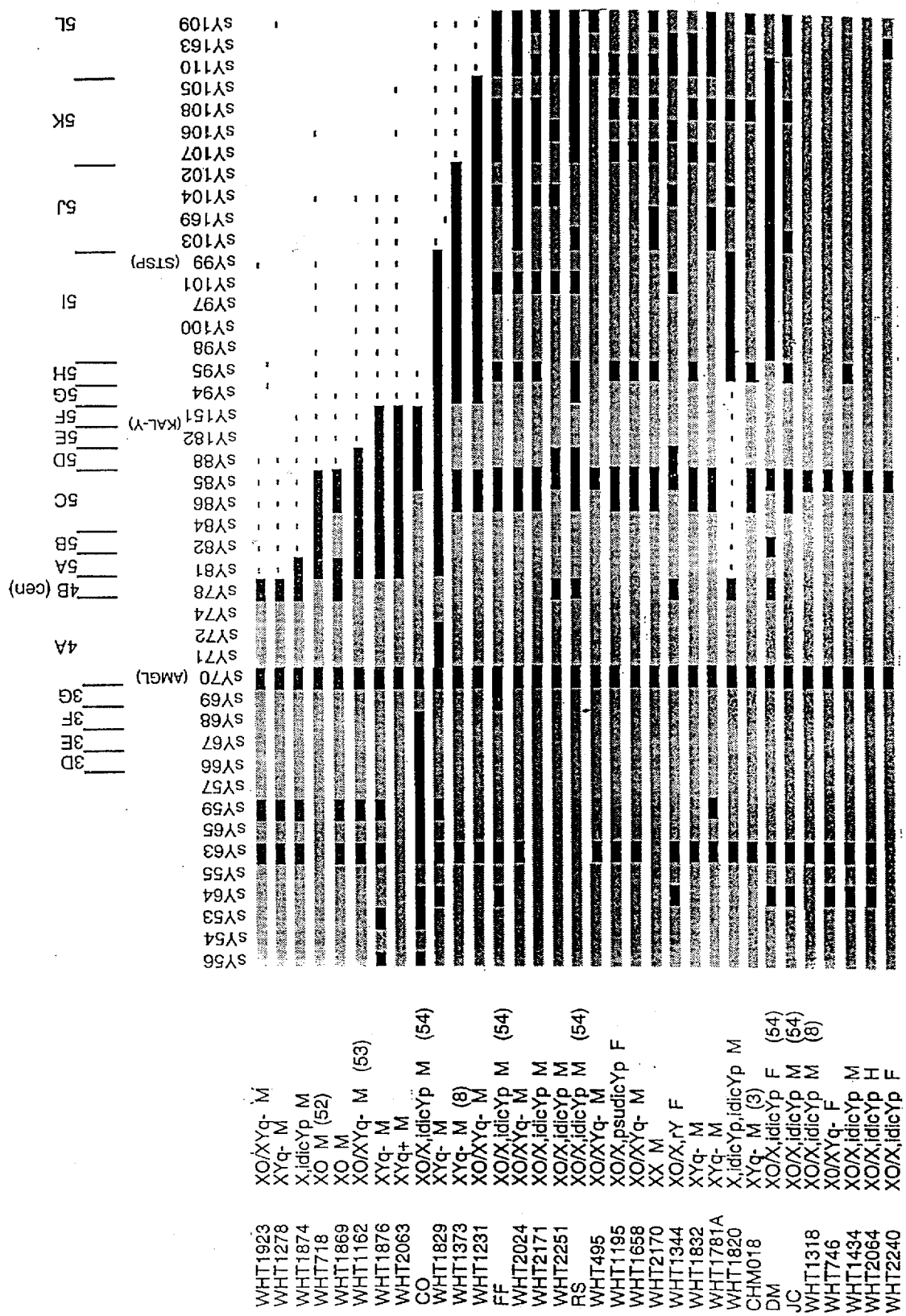
Figure 4F:
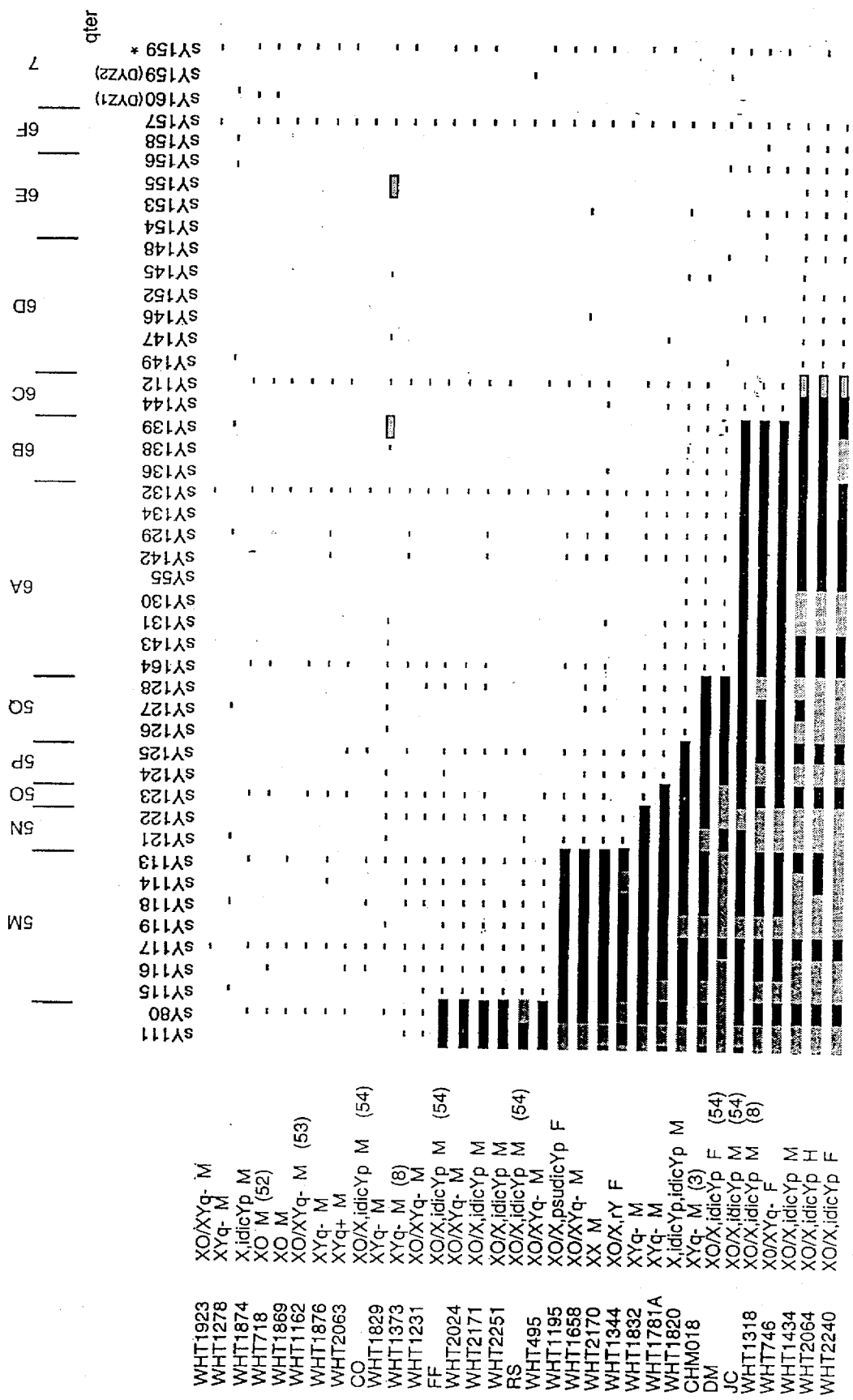
Figure 4G:
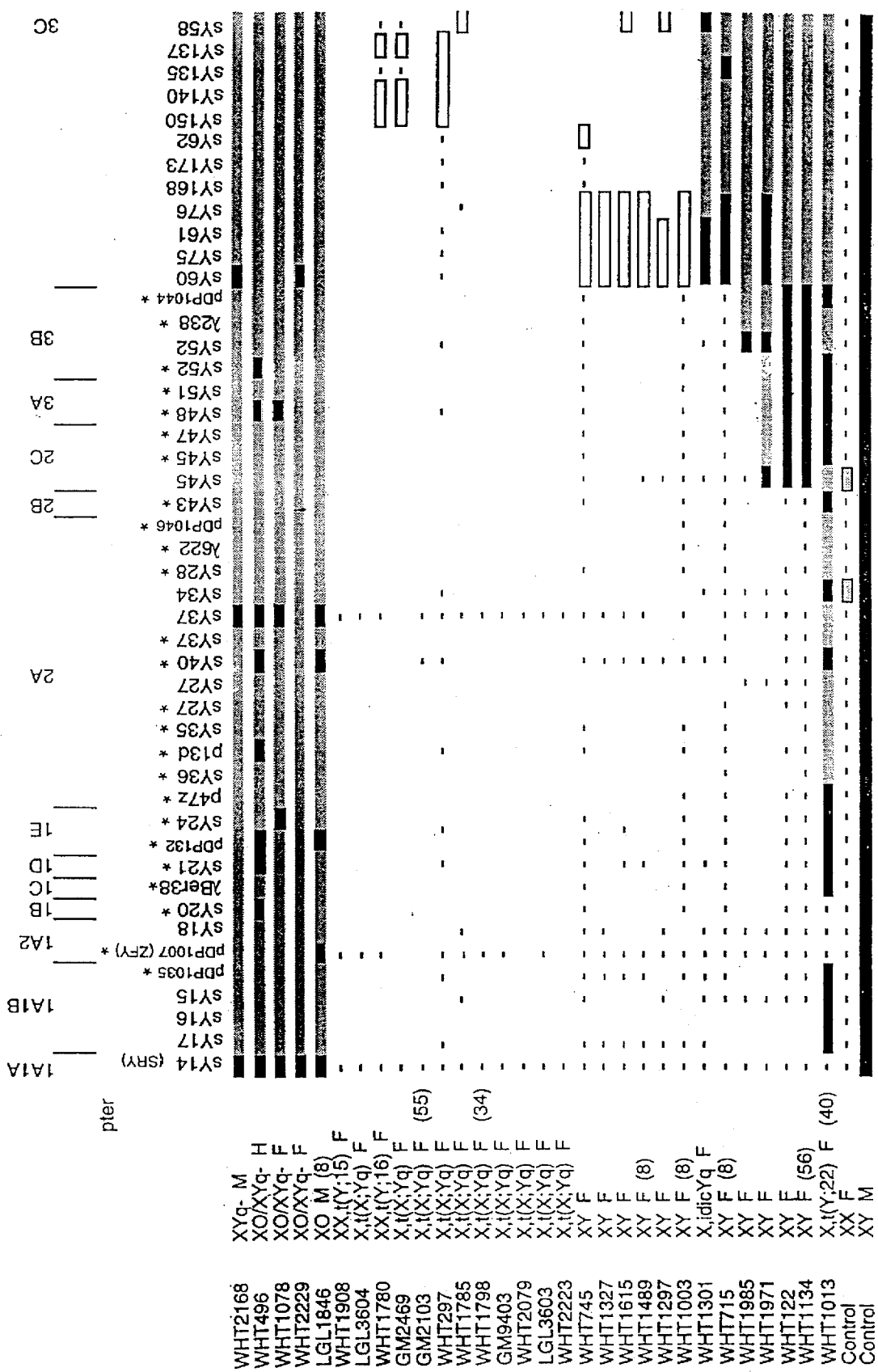
Figure 4H:
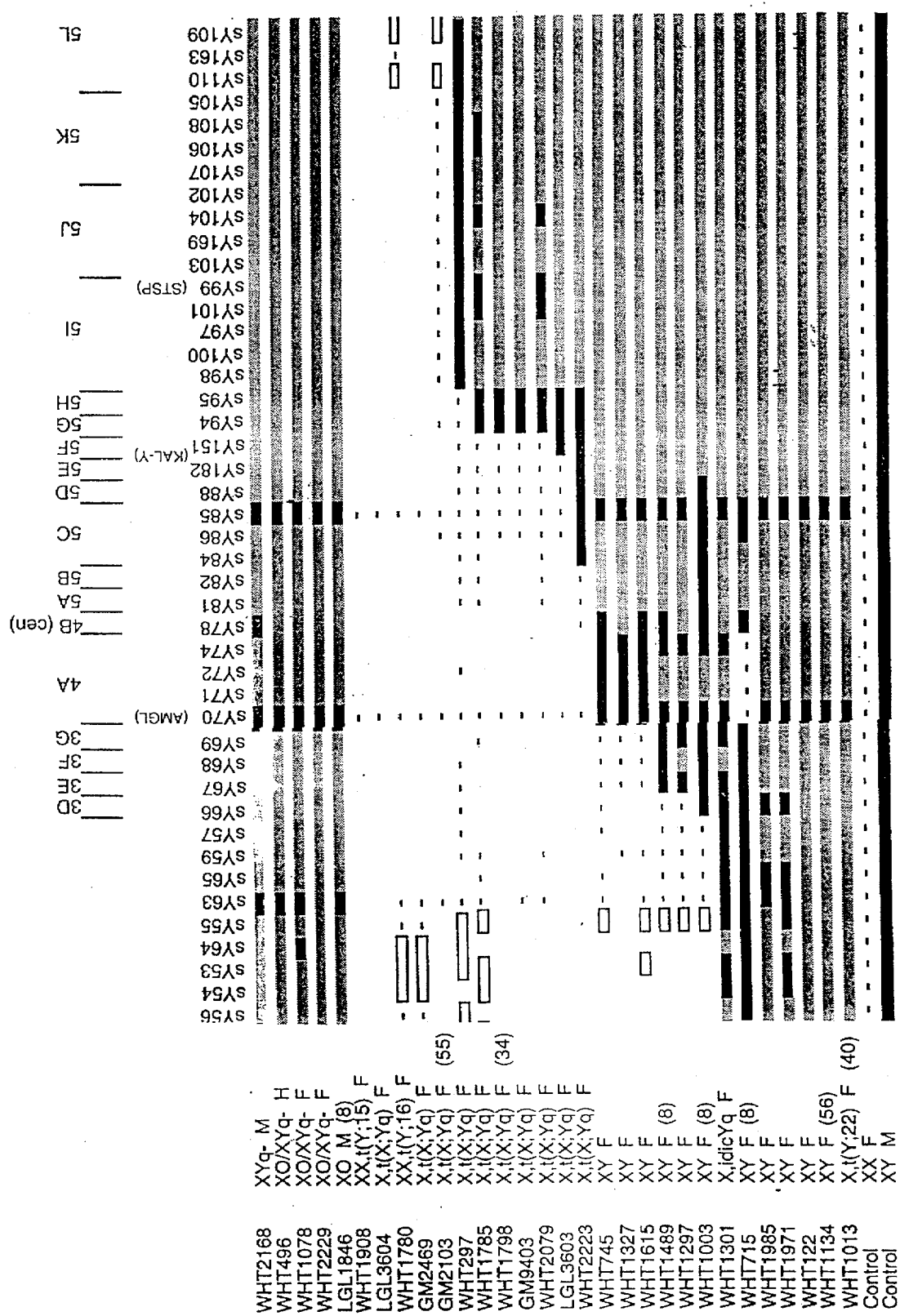
Figure 4I:
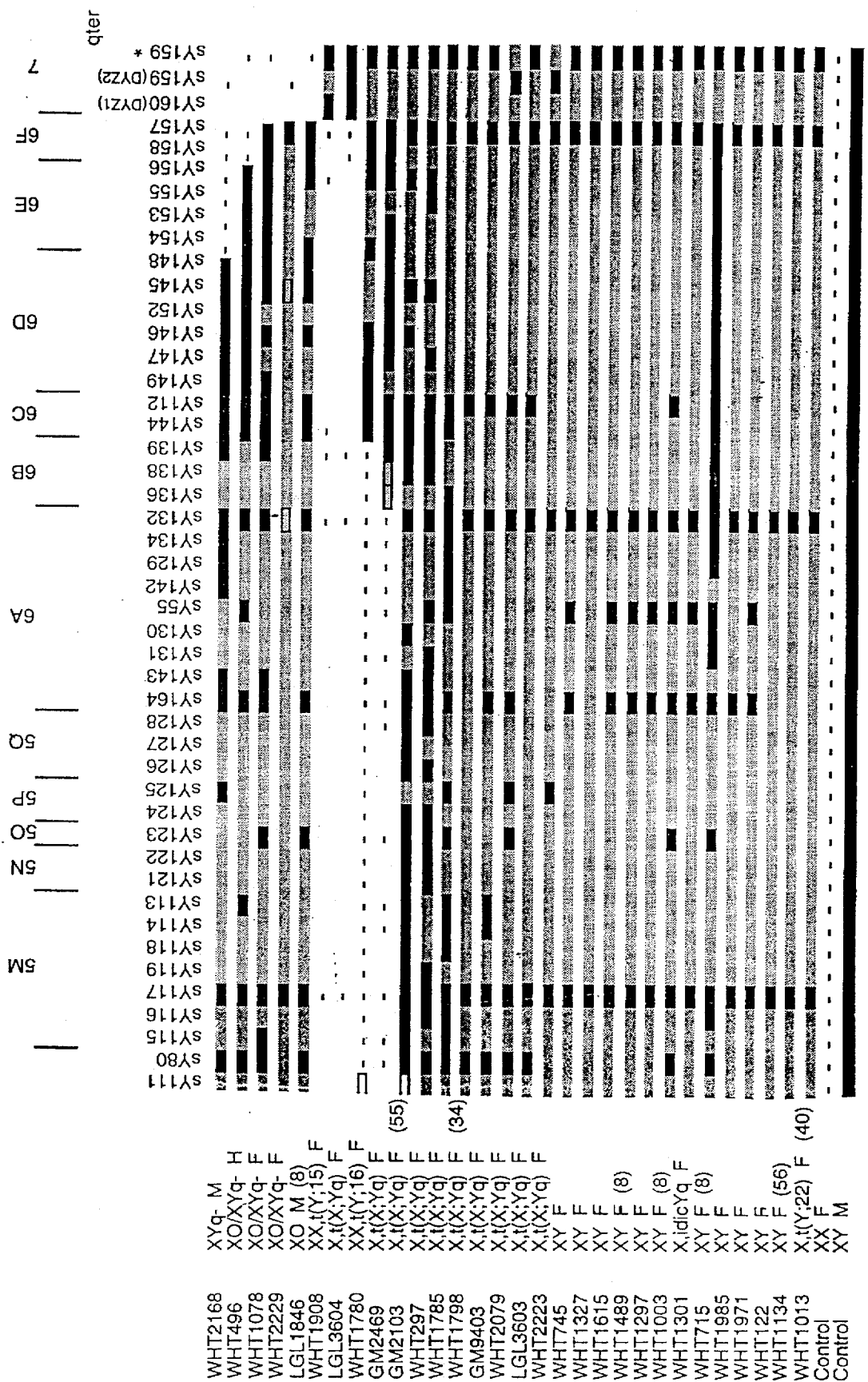

In order to identify the gene whose alteration is associated with reduced sperm count, the relevant deletion interval was analyzed for transcription units by using markers in the deletion interval, identifying YACs that span the region (see FIGS. 3A, 3B, 3C and 3D), obtaining 5-fold cosmid coverage of the interval, and using exon-trapping of cosmids to identify sequences with coding potential.

The present invention also pertains to novel methods for diagnosing and treating reduced sperm count associated with an alteration of the gene of the present invention. The present invention also has utility as a research tool, since the gene described herein, or a portion thereof, serves as a marker for the 6E deletion interval of the long arm of the Y chromosome to which it is localized. The gene of the present invention has been designated the DAZ gene. A partial nucleic acid sequence of the gene is shown in FIGS. 1 and 2 (SEQ ID NOS.: 1 and 3).

Terms used throughout the Specification are understood to have their art-recognized meaning unless otherwise defined. As used herein, the term "alteration of the gene" includes disruption of the gene (deletion of one or more nucleotides, addition of one or more nucleotides, or change in one or more nucleotides) and loss of the gene. Furthermore, azoospermia is defined as a condition wherein the concentration of sperm in a semen sample is 0 to occasional sperm per ml, and oligospermia is defined as a condition wherein the concentration of sperm in a semen sample ranges from occasional to less than 20 million per ml. Reduced sperm count is understood to encompass both oligospermia and azoospermia, i.e., a sperm count of less than 20 million per ml, including total absence of sperm.

The gene of the present invention was identified by searching the deletion interval for transcription units by combining additional new markers with known markers over the deletion interval, identifying yeast artificial chromosomes (YACs) which span the region, obtaining five-fold cosmid coverage of the interval and using exon-trapping of cosmids to identify sequences with coding potential. Once this candidate gene was identified, it was characterized to determine if it fit the profile of a gene whose alteration is associated with reduced sperm count. As described further below, the gene of the present invention is located exclusively within the deletion interval, has a testis-specific transcript and is present in a single copy on the Y chromosome.

The present invention also includes the nucleotide sequences described herein, or their complements, which are useful as hybridization probes or primers for an amplification method, such as polymerase chain reaction (PCR), to show the presence, absence or disruption of the gene of the present invention. Probes and primers can have all or a portion of the nucleic acid sequence of the gene described herein or all or a portion of its complement. For example, sequences shown in Table 1 (SEQ. ID NO. 4–9) can be used. The probes and primers can be any length, provided that they are of sufficient length and appropriate composition (i.e., appropriate nucleic acid sequence) to hybridize to all or an identifying or characteristic portion of the gene described or to a disrupted form of the gene, and remain hybridized under the conditions used.

In one embodiment, the present invention is a method of diagnosis of reduced sperm count associated with an alteration in the gene referred to herein as the DAZ gene. Any man may be assessed with this method of diagnosis. In general, the man will have been at least preliminarily assessed, by another method, as having a reduced sperm count. By combining probes derived either from the isolated native sequence of the gene, or from the primers disclosed in Table 2, with the DNA from a sample to be assessed, under conditions suitable for hybridization, it can be determined whether the patient possesses the intact gene. If the gene is unaltered, it may be concluded that the alteration of the gene is not responsible for the reduced sperm count. This invention may also be used in a similar method wherein the hybridization conditions are such that the probes will hybridize only with altered DNA and not with unaltered sequences. The hybridized DNA can also be isolated and sequenced to determine the precise nature of the alteration associated with the reduced sperm count. DNA assessed by the present method can be obtained from a variety of tissues and body fluids, Such as blood or semen. In one embodiment, the above methods are carried out on a blood DNA sample.

This invention also has utility in methods of treating disorders of reduced sperm count associated with alteration of the gene. It may be used in a method of gene therapy, whereby the gene or a gene portion encoding a functional protein is inserted into cells in which the functional protein is expressed and from which it is generally secreted to remedy the deficiency caused by the defect in the native gene.

The present invention is also related to antibodies which bind the protein encoded by the intact gene, as well as antibodies which bind the protein encoded by a disrupted gene. Such antibodies are useful as diagnostics for the intact or disrupted gene, and also as research tools for identifying either the intact or disrupted gene.

The invention will be further illustrated by the following non-limiting exemplifications:

EXAMPLES

Blood samples were obtained from 71 infertile human males who had testes biopsies. These biopsies showed 32 patients with Sertoli-cell only syndrome, 30 patients with Testicular Maturation Arrest, and 3 patients with both Sertoli-cell only and Testicular Maturation Arrest. Six additional undiagnosed azoospermic males were examined as well. Sequence-tagged sites (STS) from existing Y chromosome maps (Foote, et al., *Science,* 258: 60–66, (1992)), were incorporated with new STSs to serve as markers to assay. The Y chromosomes of the 71 patients were studied for abnormalities, especially deletions. The presence of each marker was determined by polymerase chain reaction (PCR) amplification and scoring the presence of the product after agarose gel electrophoresis. The PCR conditions consisted of a 5 minute cycle at 94° C., 35 cycles consisting of 1 minute at 94° C., 1.5 minutes at 58° C. and 1 minute at 72° C., and a final 5 minutes at 72° C. Absence of a marker indicated deletion of the region of the chromosome corresponding to that STS. Nine patients were found to have deletions in the Y chromosome. Six of the fathers of these 9 males were screened and no deletions were found, indicating a de novo mutation. The deletions in 8 of the 9 patients were found to be overlapping and within the 6E and/or D deletion interval of the Y chromosome (D. Vollrath et al., *Science*, 258: 52–59 (1992)). The one non-overlapping deletion was more proximal on the chromosome, possibly indicative of another gene or region for future study.

Yeast artificial chromosomes (YACs) that spanned the 6E interval were identified. The ends of these YACs were sequenced by ABI automated sequencing to isolate new markers to refine the Y chromosome maps. Additional markers were constructed using subtraction techniques (Rosenberg et al. (1994)). Pooled markers were then used as probes to obtain 5-fold cosmid coverage from the Lawrence Livermore Chromosome Y Cosmid Library LLOYCN03"M". This produced 124 cosmids, 76% of which contain STSs that fall in the 6E deletion interval. Sixty cosmids were subcloned from yOX17, a 920-kb YAC spanning most of the deletion region. Three P1 clones containing marker sy202 were obtained from Genome Systems to provide fuller coverage of the distal region.

Cosmid #316 (Lawrence Livermore address: Plate 35, row G, column 3), cosmid #325 (Lawrence Livermore address: Plate 48, row D, column 5) and cosmid #330 (Lawrence Livermore address: Plate 59, row H, column 4) were obtained by hybridization. These cosmids were subcloned into exon-trapping vector pSPL3, a vector containing splice donor and acceptor sites. This vector was then transfected into mammalian COS-7 cells according to the exon-trapping system of GibcoBRL/Life Technologies, Cat. No. 18449-017. The exon-trapped exons were then amplified and sequenced using polymerase chain reactions (PCR) and automated sequencing.

The results of the exon-trapping and sequencing indicated that there was one clear cut transcription unit in the interval of interest. The blood DNA of the 8 patients was then probed with a pair of primers from within the gene to confirm that this sequence was indeed missing in males with reduced sperm count. Table 1 list primers used to confirm that this gene is missing in infertile men with reduced sperm counts. Study of tissue from the spleen, thymus, prostate, ovary, small intestine, colon, leukocytes and testis indicate that the DAZ transcript is primarily expressed in the testis.

nucleotide sequences of these cDNAs (#66B and 98B) and the corresponding amino acid sequences are shown in FIG. 1 (SEQ ID NOS.: 1 and 2) and FIG. 2 (SEQ ID NO.: 3).

The sequenced exons were also analyzed by GRAIL, FASTN and BLAST to identify potential coding regions and/or homology with known sequences. From this resulting data, it was determined that the DAZ gene is a member of the gene family encoding RNA binding proteins such as poly-A binding protein, hnRNPa1, sex lethal, and a previously identified Y-chromosome gene, YRRM. The nucleotide sequence bears little resemblance to any of these family members, but the RNA binding domains are conserved at the protein level. The closest relative appears to be poly-A binding protein (see Table 2).

TABLE 2

| | RNA Binding Domain | |
|---|---|---|
| | RNP2 | RNP1 |
| RNA BINDING CONSENSUS SEQUENCE: | LFVGNLA (SEQ ID NO: 10) or IYIKGM (SEQ ID NO: 11) | KGYGFVXF (SEQ ID NO: 13) |
| POLY-A BINDING PROTEIN | LFVGNL (SEQ ID NO: 12) | KGYGFVNF (SEQ ID NO: 14) |
| DAZ | LFVGGI | KGYGFVSF (SEQ ID NO: 15) |

The results of a Northern Blot performed on the exons obtained from exon-trapping showed that the total gene is approximately 3.1 kb. The three cDNAs currently sequenced, #66B, 93B and 98B (pDP #1575, #1576 and #1577), contain a total of 2.5 kb of the sequence. The rest of the sequence can be obtained by probing a the Clonetech 9enomic adult human cDNA λDR2 testes library with the ends of the known sequences and using PCR to amplify and sequence the sequence obtained thereby.

Equivalents

Those skilled in the art will recognize or be able to ascertain, using no more than routine experimentation, many

TABLE 1

| OLIGO NO. | SEQUENCE | EXON CLONE# | PAIR WITH | PRODUCT SIZE | Yspec. larger | sY No. |
|---|---|---|---|---|---|---|
| 3115 | GGGTGTTACCAGAAGGCAA (SEQ ID NO: 4) | ET316-13;-10 | 3116 | 400 | yes | 254 |
| 3116 | GAACCGTATCTACCAAAGCAGC (SEQ ID NO: 5) | ET316-13;10 | 3115 | 400 | | |
| 3123 | GTTACAGGATTCGGCGTGAT (SEQ ID NO: 6) | ET325-17 | 3124 | 125 | yes | 258 |
| 3124 | CTCGTCATGTGCAGCCAC (SEQ ID NO: 7) | ET325-17 | 3123 | 125 | | |
| 3125 | GCTGCAAATCCTGAGACTCC (SEQ ID NO: 8) | 330-13/23 | 3126 | 102 | yes | 259 |
| 3126 | TTTGCCTTCTGGTAACACCC (SEQ ID NO: 9) | 330-13/23 | 3125 | 102 | | |

The sequenced exons produced by the exon-trapping system were then used in a hybridization screen against a Clonetech genomic adult human cDNA λDR2 testes library. One hundred cDNAs were obtained, and two, which contained the same primer bands (#3115-16 and #3125-26) as seen in the original blood sample, were sequenced. The equivalents to the specific embodiments of the invention described specifically herein. Such equivalents are intended to be encompassed in the scope of the following claims.

The invention claimed is:

1. A method of diagnosing reduced sperm count associated with alteration of a DAZ gene present in interval 6E of the distal portion of the long arm of the human Y chromosome, comprising the steps of:
   a) obtaining a DNA sample to be assessed;
   b) processing the DNA sample such that the DNA is available for hybridization;
   c) combining the DNA of step (b) with nucleotide probes complementary to the DNA sequence of the DAZ gene and comprising at least 14 consecutive nucleotides of SEQ ID NO: 1 or SEQ ID NO: 3, under conditions appropriate for specific hybridization of the probes with complementary nucleotide sequences in the DNA sample, thereby producing a combination; and
   d) detecting hybridization in the combination, wherein absence of hybridization in the combination is indicative of reduced sperm count associated with an alteration of a DAZ gene present in interval 6E of the distal portion of the Y chromosome.

2. A method of diagnosing reduced sperm count associated with alteration of a DAZ gene present in interval 6E of the distal portion of the long arm of the human Y chromosome, comprising the steps of:
   a) obtaining a DNA sample to be assessed;
   b) processing the DNA sample such that the DNA is available for hybridization;
   c) combining the DNA of step (b) with nucleotide sequences complementary to the DNA sequence of a DAZ gene present in interval 6E of the distal portion of the long arm of the human Y chromosome, whose alteration is associated with reduced sperm count, said nucleotide sequences comprising nucleotide sequences selected from the group consisting of:
i) SEQ ID NO: 4;
ii) the complement of SEQ ID NO: 4;
iii) SEQ ID NO: 5;
iv) the complement of SEQ ID NO: 5;
v) SEQ ID NO: 6;
vi) the complement of SEQ ID NO: 6;
vii) SEQ ID NO: 7;
viii) the complement of SEQ ID NO: 7;
ix) SEQ ID NO: 8;
x) the complement of SEQ ID NO: 8;
xi) SEQ ID NO: 9; and
xii) the complement of SEQ ID NO: 9,
under conditions appropriate for specific hybridization of the probes with complementary nucleotide sequences in the DNA sample, thereby producing a combination; and
d) detecting hybridization in the combination, wherein absence of hybridization in the combination is indicative of reduced sperm count associated with an alteration of a DAZ gene present in interval 6E of the distal portion of the Y chromosome.

3. The method of claim 2, wherein the alteration is deletion of all or a portion of the gene.

4. A method of diagnosing reduced sperm count associated with alteration of a DAZ gene present in interval 6E of the distal portion of the long arm of the human Y chromosome, comprising the steps of:
a) obtaining a DNA sample to be assessed;
b) processing the DNA sample such that the DNA is available for hybridization;
c) combining the DNA of step (b) with nucleotide probes complementary to an altered DNA sequence of a DAZ gene present in interval 6E of the distal portion of the long arm of the human Y chromosome, whose alteration is associated with reduced sperm count, under conditions appropriate for specific hybridization of the probes with the altered DNA sequence of a DAZ gene present in interval 6E of the distal portion of the long arm of the human Y chromosome, in the DNA sample, but not with an unaltered DNA sequence of a DAZ gene present in interval 6E of the distal portion of the long arm of the human Y chromosome, thereby producing a combination; and
d) detecting hybridization in the combination, wherein presence of hybridization in the combination is indicative of reduced sperm count associated with an alteration of a DAZ gene present in interval 6E of the distal portion of the Y chromosome.

5. The method of claim 2, wherein the DNA sample is derived from blood.

6. A method of diagnosing reduced sperm count associated with alteration of a DAZ gene present in interval 6E and/or 6D of the distal portion of the long arm of the human Y chromosome, comprising the steps of:
a) obtaining a DNA sample to be assessed;
b) processing the DNA sample such that the DNA is available for hybridization;
c) combining the DNA of step (b) with nucleotide probes complementary to the DNA sequence of the DAZ gene and comprising at least 14 consecutive nucleotides of SEQ ID NO: 1 or SEQ ID NO: 3, under conditions appropriate for specific hybridization of the probes with complementary nucleotide sequences in the DNA sample, thereby producing a combination; and
d) detecting hybridization in the combination, wherein absence of hybridization in the combination is indicative of reduced sperm count associated with an alteration of a DAZ gene present in interval 6E and/or 6D of the distal portion of the Y chromosome.

7. A method of diagnosing reduced sperm count associated with alteration of a DAZ gene present in interval 6E and/or 6D of the distal portion of the long arm of the human Y chromosome, comprising the steps of:
a) obtaining a DNA sample to be assessed;
b) processing the DNA sample such that the DNA is available for hybridization;
c) combining the DNA of step (b) with nucleotide sequences complementary to the DNA sequence of a DAZ gene present in interval 6E and/or 6D of the distal portion of the long arm of the human Y chromosome, whose alteration is associated with reduced sperm count, said nucleotide sequences comprising nucleotide sequences selected from the group consisting of:
i) SEQ ID NO: 4;
ii ) the complement of SEQ ID NO: 4;
iii) SEQ ID NO: 5;
iv) the complement of SEQ ID NO: 5;
v) SEQ ID NO: 6;
vi) the complement of SEQ ID NO: 6;
vii) SEQ ID NO: 7;
viii) the complement of SEQ ID NO: 7;
ix) SEQ ID NO: 8;
xi) the complement of SEQ ID NO: 8;
xi) SEQ ID NO: 9; and
xii) the complement of SEQ ID NO: 9,
under conditions appropriate for specific hybridization of the probes with complementary nucleotide sequences in the DNA sample, thereby producing a combination; and
d) detecting hybridization in the combination, wherein absence of hybridization in the combination is indicative of reduced sperm count associated with an alteration of a DAZ gene present in interval 6E and/or 6D of the distal portion of the Y chromosome.

8. A method of diagnosing reduced sperm count associated with alteration of a DAZ gene present in interval 6E and/or 6D of the distal portion of the long arm of the human Y chromosome, comprising the steps of:
a) obtaining a DNA sample to be assessed;
b) processing the DNA sample such that the DNA is available for hybridization;
c) combining the DNA of step (b) with nucleotide probes complementary to an altered DNA sequence of a DAZ gene present in interval 6E and/or 6D of the distal portion of the long arm of the human Y chromosome, whose alteration is associated with reduced sperm count, under conditions appropriate for specific hybridization of the probes with the altered DNA sequence of a DAZ gene present in interval 6E and/or 6D of the distal portion of the long arm of the human Y chromosome; in the DNA sample, but not with an unaltered DNA sequence of a DAZ gene present in interval 6E and/or 6D of the distal portion of the long arm of the human Y chromosome, thereby producing a combination; and
d) detecting hybridization in the combination, wherein presence of hybridization in the combination is indicative of reduced sperm count associated with an alteration of a DAZ gene present in interval 6E and/or 6D of the distal portion of the Y chromosome.

9. A method of diagnosing reduced sperm count associated with alteration of a DAZ gene comprising SEQ ID NO: 1 and/or SEQ ID NO: 3 and present in interval 6E and/or 6D of the distal portion of the long arm of the human Y chromosome, comprising the steps of:

a) obtaining a DNA sample to be assessed;

b) processing the DNA sample such that the DNA is available for hybridization;

c) combining the DNA of step (b) with nucleotide probes complementary to the DNA sequence of the DAZ gene comprising SEQ ID NO: 1 and comprising at least 14 consecutive nucleotides, under conditions appropriate for specific hybridization of the probes with complementary nucleotide sequences in the DNA sample, thereby producing a combination; and d) detecting hybridization in the combination, wherein absence of hybridization in the combination is indicative of reduced sperm count associated with an alteration of a DAZ gene comprising SEQ ID NO: 1 and present in interval and/or 6D of the distal portion of the Y chromosome.

10. A method according to claim 9, wherein the DAZ gene further comprises SEQ ID NO: 3.

11. A method of diagnosing reduced sperm count associated with alteration of a DAZ gene comprising SEQ ID NO: 1 and present in interval 6E and/or 6D of the distal portion of the long arm of the human Y chromosome, comprising the steps of:

a) obtaining a DNA sample to be assessed;

b) processing the DNA sample such that the DNA is available for hybridization;

c) combining the DNA of step (b) with nucleotide sequences complementary to the DNA sequence of a DAZ gene comprising SEQ ID NO: 1 and prosone in interval 6E and/or 6D of the distal portion of the long arm of the human Y chromosome, whose alteration is associated with reduced sperm count, said nucleotide sequences comprising nucleotide sequences selected from the group consisting of:

i) SEQ ID NO: 4;
ii) the complement of SEQ ID NO: 4;
iii) SEQ ID NO: 5;
iv) the complement of SEQ ID NO: 5;
v) SEQ ID NO: 6;
vi) the complement of SEQ ID NO: 6;
vii) SEQ ID NO: 7;
viii) the complement of SEQ ID NO: 7;
ix) SEQ ID NO: 8;
x) the complement of SEQ ID NO: 8;
xi) SEQ ID N0: 9; and
xii) the complement of SEQ ID. NO: 9, under conditions appropriate for hybridization of the probes with complementary nucleotide sequences in the DNA sample, thereby producing a combination; and d) detecting hybridization in the combination, wherein absence of hybridization in the combination is indicative of reduced sperm count associated with an alteration of a DAZ gene comprising SEQ, ID NO: 1 and present in interval 6E and/or 6D of the distal portion of the Y chromosome.

12. A method according to claim 11, wherein the DAZ gene further comprises SEQ ID NO: 3.

13. A method of diagnosing reduced sperm count associated with alteration of a DAZ gene comprising SEQ ID NO: 1 and/or SEQ ID NO: 3 and present in interval 6E and/or 6D of the distal portion of the long arm of the human Y chromosome, comprising the steps of:

a) obtaining a DNA sample to be assessed;

b) processing the DNA sample such that the DNA is available for hybridization;

c) combining the DNA of step (b) with nucleotide probes complementary to an altered DNA sequence of a DAZ gene present in interval 6E and/or 6D of the distal portion of the long arm of the human Y chromosome, whose alteration is associated with reduced sperm count, under conditions appropriate for specific hybridization of the probes with the altered DNA sequence of a DAZ gene present in interval 6E And/or 6D of the distal portion of the long arm of the human Y chromosome, in the DNA sample, but not with an unaltered DNA sequence of a DAZ gene present in interval 6E and/or 6D of the distal portion of the long arm of the human Y chromosome, thereby producing a combination; and d) detecting hybridization in the combination, wherein presence of hybridization in the combination is indicative of reduced sperm count associated with an alteration of a DAZ gene comprising SEQ ID NO: 1 and present in interval 6E and/or 6D of the distal portion of the Y chromosome.

14. A method according to claim 13, wherein the DAZ gene further comprises SEQ ID NO: 3.

* * * * *

UNITED STATES PATENT AND TRADEMARK OFFICE
CERTIFICATE OF CORRECTION

PATENT NO. : 5,695,935
DATED : December 9, 1997
INVENTOR(S) : David C. Page and Renee Reijo It is certified that error appears in the above-identified patent and that said Letters Patent is hereby corrected as shown below:

In column 6, lines 35-37, please delete "The rest of the sequence can be obtained by probing a the Clonetech 9enomic" and insert therefor --The rest of the sequence can be obtained by probing a Clonetech genomic--.

Signed and Sealed this

Tenth Day of April, 2001

Attest:

NICHOLAS P. GODICI

*Attesting Officer*  *Acting Director of the United States Patent and Trademark Office*